United States Patent [19]

Mills

[11] Patent Number: 4,979,504
[45] Date of Patent: * Dec. 25, 1990

[54] ORAL IRRIGATOR

[76] Inventor: Herbert J. Mills, 14 Whieldon La., Worthington,, Ohio 43085

[*] Notice: The portion of the term of this patent subsequent to Oct. 25, 2004 has been disclaimed.

[21] Appl. No.: 819,436

[22] Filed: Jan. 16, 1986

[51] Int. Cl.$^5$ .................. A61H 9/00; A61M 31/00; A61G 5/02
[52] U.S. Cl. .................. 128/66; 604/73; 604/77; 433/81
[58] Field of Search .................. 433/80, 32, 81; 417/394; 222/95; 128/62 A, 66; 604/77, 73; 401/139, 286, 289, 291

[56] References Cited

U.S. PATENT DOCUMENTS

| | | | |
|---|---|---|---|
| 1,868,893 | 7/1932 | Gentle | 128/62 A |
| 2,187,560 | 1/1940 | Reilly | 128/62 A |
| 3,199,510 | 8/1965 | Sinai | 128/62 A |
| 3,214,775 | 11/1965 | Morov et al. | 128/66 |
| 3,225,759 | 12/1965 | Drapon et al. | 128/62 A |
| 3,509,874 | 5/1970 | Stillman | 128/66 |
| 3,739,983 | 6/1973 | Jousson | 128/66 |
| 3,747,216 | 7/1973 | Bassi et al. | 433/81 |
| 4,270,533 | 6/1981 | Andrews | 222/95 |

Primary Examiner—John D. Yasko
Assistant Examiner—J. L. Kruter
Attorney, Agent, or Firm—John L. Gray

[57] ABSTRACT

An oral irrigator for lavaging all of the gingival crevice including the interdental area of the gums, provided with a tip at the end of a probe for separating the gum part known as the gingival collar from the facial or linqual and interproximal sides of the tooth and having a steady flow of antimicrobial fluid expelled from a zone surrounding said tip. Also shown is such an oral irrigator in combination with a tap water, pressure operated, germicidal-containing container forcing germicidal fluid through said oral irrigator tip, and with a tap water syphon delivery system.

5 Claims, 2 Drawing Sheets

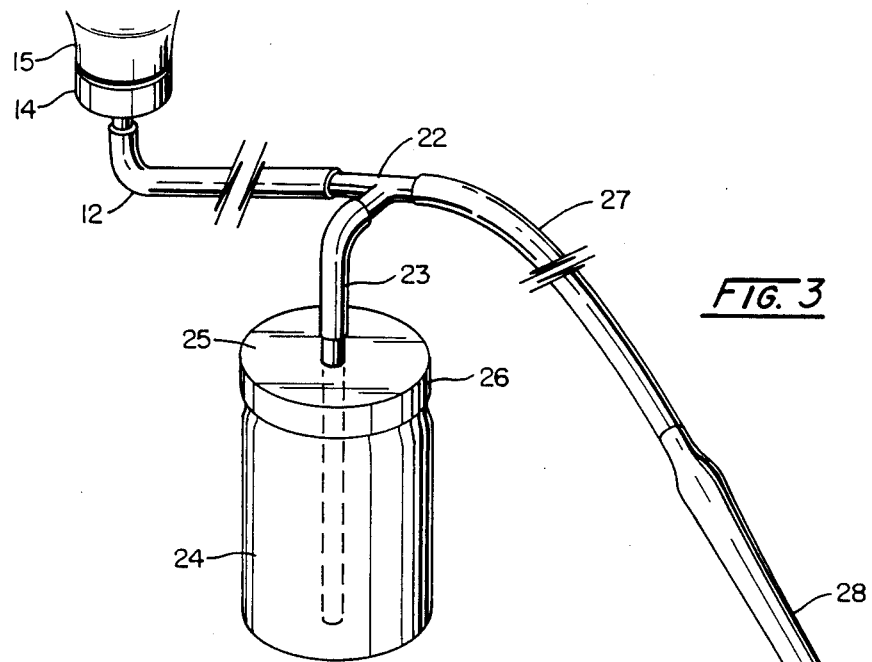
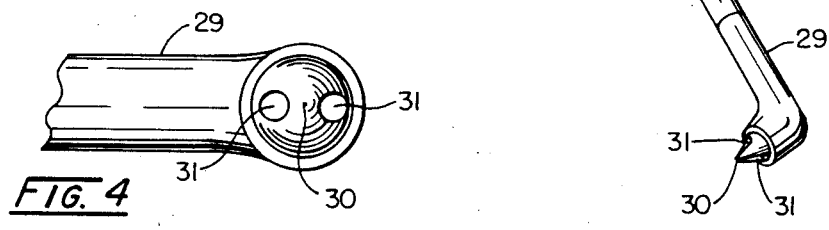
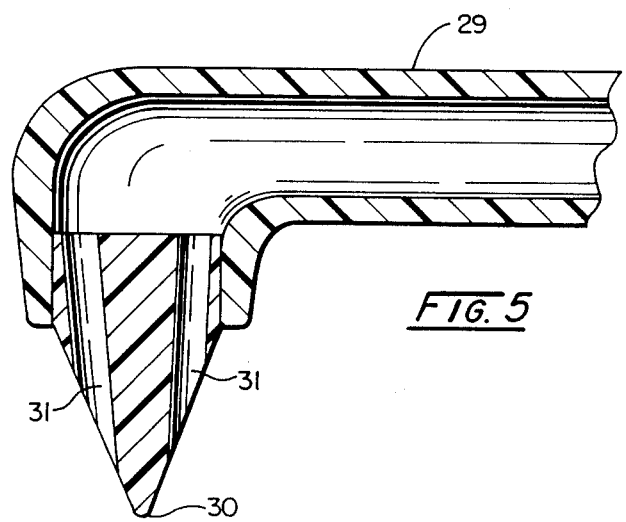

ORAL IRRIGATOR

BACKGROUND OF THE INVENTION

Plastic lavaging devices for oral hygiene conveying a pulsating fluid to the rounded blunt tip of the lavage wand are well-known in the art. Typical are U.S. Pat. Nos. 3,393,673, Mattingly; 3,227,158, Mattingly; and 3,425,410, Cammack. In some instances, the fluid is not dispensed through the tip of the wand but instead is dispensed adjacent the tip. Examples of these are U.S. Pat. Nos. 3,645.255, Robinson; and 4,173,828, Lustig, et al. In some cases, the pulsating electric motor driven units are replaced with devices that are directly connected to a faucet, relying on household water pressure for flow. Examples of these are U.S. Pat. Nos. 3,465,751, Powers; 4,135,501, Leunissan; and 3,593,707, Pifer.

In addition, there are oral hygienic devices in which carie attacking chemicals or other liquids may be dispensed from a container in addition to the flow of water through the applicator. Examples of these are U.S. Pat. Nos. 4,012,842, Vit; 4,422,450, Rusteberg; 4,452,238, Kerr; 4,173,828, Lustig, et al.; and 3,675,645, Samiran, et al.

Recent research has shown that most periodontal disease begins and becomes well-established in the interproximal area more often than on the facial or linqual sides of the tooth. In fact, periodontal disease is mainly an interproximal disease. Devices of the prior art, especially those directed to tips or probe design, attempt to clean the facial or linqual sides of the tooth, rather than to flush out the space which is the gingival sulcus. Existing irrigating devices emphasize a very narrow stream of water flowing at high velocity. High pressure is developed in the barrel of the device to create this high velocity. Using such a system, the amount of irrigation solution, which actually washes the tooth surface at the tooth gum margin is minimal, about 125 to 150 ml./min. The pulsating devices of the prior art are utilized supposedly to deflect the gum tissue surrounding the tooth, thereby exposing the tooth surface adjacent to the gingival sulcus. The theory is that the high pressure, pulsating stream deflects the gum tissue around the tooth, thus providing access to the sulcus surrounding the tooth; however, many people who use these devices still experience gum bleading and other signs of active gum disease.

Previous emphasis of lavaging devices has been the removal of food debris from the surfaces of the teeth above the gum line. While this may be helpful to avert tooth decay, research is demonstrating that daily degerming of the mouth is especially necessary to limit and manage periodontal disease. The presence of certain harmful anaerobic bacteria in the ecological niche of the gingival sulcus appears to be the major factor in the prevalence of periodontal disease in an individual.

Around each tooth, at the gum line, is a circular band of fibers called the gingival collar which is also known as the gingival cuff. This sturdy structure forms the top of the gingival sulcus or in the diseased state it would be the top of the gingival pocket. This structure acts as a barrier to the penetration of antimicrobial lavage water into the gingival sulcus. Adequate degerming of the sulcus requires physical displacement of the gingival collar away from the tooth surface which enlarges the space known as the gingival sulcus and permits copious amounts of antimicrobial lavaging to disperse, disorganize, and to detoxify the coating of plaque which forms in the ecological niche known as the sulcus.

Pulsations also interfere with the ability of the user to accurately trace the gum margin. The recoil from the pulsation overrides the feedback which provides contact to the hand of the user. In addition, the intermittant spraying from the pulsation adds to this sensory confusion.

SUMMARY OF THE INVENTION

The oral irrigator of the instant invention is designed to physically deflect the parts of the gum called the gingival collar and to lavage the papillary area and sulcus thus exposed with a maximum amount of lavaging antimicrobial fluid. A steady, non-pulsating stream, accurately directed into the sulcus is the most effective method of degerming the sulcus. In addition, since there is no vibration from pulsating fluid, it is much easier to direct the tip of the probe of the instant invention by direct contact with the extremely narrow band of gum at the sulcus margin.

It is therefore an object of this invention to provide an oral irrigator which enables a large volume of antimicrobial fluid to be directed directly into the interproximal papilla and entire gingival sulcus.

It is a further object of this invention to provide such a device which does not solely require an electrical connection and the operation of a pulsating motor.

It is still another object of this invention to provide a device of this type which may be used to cause a flow of anti-microbial fluid into the interdental papilla and sulcus in order to emphasize degerming of the mouth and special ecological niches of anaerobic bacteria as contrasted with simple removal of food debris.

These, together with other objects and advantages of the invention, should become apparent in the details of construction and operation as more fully described hereinafter and claimed, reference being had to the accompanying drawings forming a part hereof wherein like numerals refer to like parts throughout.

BRIEF DESCRIPTION OF THE DRAWINGS

FIG. 3 is a perspective view of the instant invention showing a variation on the means of drawing antimicrobial fluid from a dispensing unit.

FIG. 4 is a plan view of a variation of the probe tip and is the one shown in FIG. 3.

FIG. 5 is a side elevation sectional view of the probe tip shown in FIG. 4.

DETAILED DESCRIPTION OF THE DRAWINGS

Figure 1:
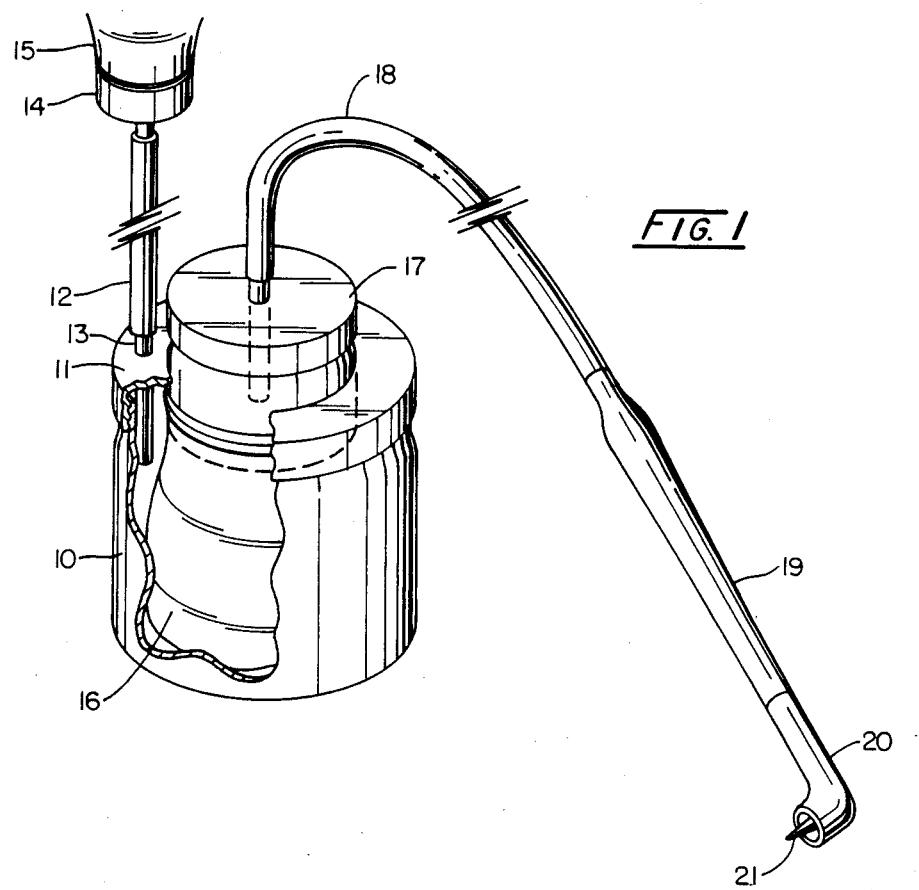
FIG. 1 is a perspective view of the instant invention showing the probe attached to a dispensing unit, which in turn may be connected to a household faucet.

Referring now more particularly to FIG. 1, a container 10 is provided with a screw top 11 adapted to receive a flexible hose 12 through opening 13, flexible hose 12 in turn is connected to adaptor 14 of a conventional-type, which may be attached to a faucet 15. A variety of such attachments are readily available and on the market. Collapsible container 16 is placed inside container 10 and is fitted with cover 17 adapted to receive a flexible hose 18. This flexible hose 18 is connected to wand 19, terminating in probe 20 which is provided with tip 21.

Figure 2:
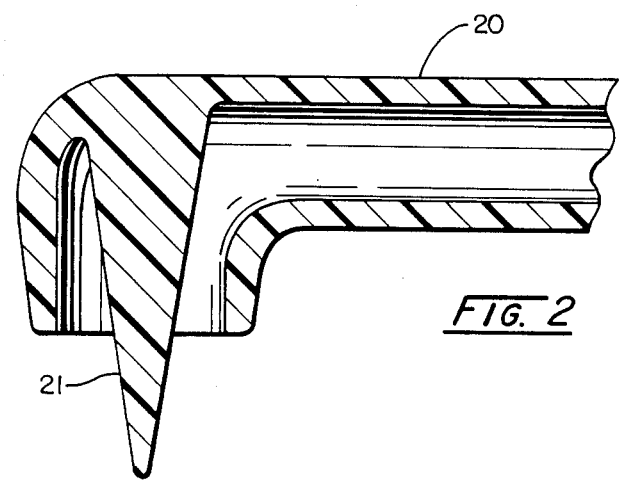
FIG. 2 is a side elevation, sectional view of the probe tip shown in FIG. 1.

Referring now more particularly to FIG. 2, it will be seen that probe 20 and tip 21 are so constructed that a maximum flow of fluid through probe 20 and around tip 21 is achieved. If desired, a valve in wand 19 may be utilized to control the flow of fluid rather than utilizing the valve controlling the fluid to the faucet 15. The probe 20 and the tip 21 may be made of a variety of materials. Among these are nylon, delrin, and polypropylene. Likewise, the probe 20 and the tip 21 may be made as a single extrusion as shown in FIG. 2.

In operation, the flow of fluid from the faucet 15 into the container 10 causes the collapsible container 16 to force the germicidal solution contained therein out and through hose 18, wand 19, probe 20, and around tip 21. For convenience of the user, probe 20 terminates in an opening at right angles to its major axis and thus the tip 21 is also positioned at right angles to the major axis of the probe 20 for ease of use. With tip 21 positioned at the extremely narrow band of gum at the sulcus margin, a large lavaging flow of antimicrobial fluid surrounding the tip 21 is achieved, thus maximizing the degerming of the sulcus.

If desired, the collapsible container 16 may be omitted, and germicidal material, which will dissolve from the action of the flow of water through container 10 may be used. This germicidal material, dissolved in water, will then be forced out of container 10 and through hose 18 to the open end of probe 20.

Referring now more particularly to FIG. 3, the faucet 15 is provided with an adaptor 14 which in turn is connected to flexible hose 12. In this instance, however, flexible hose 12 is connected to a "T" fitting, one leg of which is connected to a suction hose 23 which fits into container 24 containing the antimicrobial fluid. An air vent 25 is provided in the cover 26 on container 24. The other portion of the "T" fitting is connected to flexible hose 27 which in turn is connected to wand 28 terminating in probe 29. Probe 29 is provided with a tip 30 which extends at right angles to the major axis of the probe 29 and is provided with two openings 31—31 generally in line with the major axis of probe 29. This can be seen more readily in FIGS. 4 and 5.

In operation of this device, the flow of water from the faucet 15 will syphon antimicrobial fluid from container 24 through hose 23 and eject it through openings 31—31 adjacent tip 30. If desired, an electrical motor driven pump (not shown) can be used as an alternative The variation of the tip 30 shown in FIG. 5 as compared to the tip 21 shown in FIG. 2 is twofold. Since probe 29 is injection molded, this type of configuration permits removal from the mold more readily. It also directs the fluid through holes 31—31 adjacent to the tip 30 since the holes 31-31 are tapered inwardly toward tip 30, thus maximizing the flow of antimicrobial fluid into the desired zone.

While this invention has been described in its preferred embodiment, it is appreciated that variations thereon may be made without departing from the proper scope and spirit of the invention.

I claim:

1. An oral irrigator comprising a major horizontal extending conduit having a central lumen and having an inner and outer surface terminating in a minor portion of said conduit having a symetrical axis substantially perpendicular to said major conduit portion, a solid cone portion means axially positioned within the opening of said minor conduit and singularly integral with an inner wall of said major conduit extending outwardly beyond the terminal walls of said minor conduit, said cone portion means to deflect the gingival collar of a patient's gum so as to permit lavaging the papillary area and sulcus with an antimicrobial fluid, said minor portion of said irrigator having an internal lumen means in fluid communication with said lumen of said major conduit to direct antimicrobial fluid to the operative site, said lumen of said minor portion of said conduit complete surrounding said solid cone portion.

2. The oral irrigator of claim 1 wherein the opposite end of said conduit from said minor portion of said conduit is connected through a flexible hose to a flexible receptacle capable of containing an antimicrobial solution and means for expelling said antimicrobial solution through said flexible hose to said conduit.

3. The oral irrigator of claim 2 wherein said means for expelling said antimicrobial solution through said flexible hose to said conduit includes a flexible container provided with a container surrounding said flexible container adapted to receive fluid under pressure to compress said flexible container.

4. The oral irrigator of claim 2 wherein said means for expelling said antimicrobial solution through said flexible hose to said conduit includes a syphon.

5. The oral irrigator of claim 2 wherein said means for expelling said antimicrobial solution through said flexible hose to said conduit includes an electric motor-driven pump.

* * * * *